United States Patent [19]
Ovil

[11] Patent Number: 5,797,930
[45] Date of Patent: Aug. 25, 1998

[54] SURGICAL IMPLEMENT AND METHOD OF SUTURING

[75] Inventor: Joel Ovil, Ramat Hasharon, Israel

[73] Assignee: Dan Siev, Kfar Shmaryahu, Israel; a part interest

[21] Appl. No.: 772,586

[22] Filed: Dec. 26, 1996

[51] Int. Cl.$^6$ .................................................. A61B 17/04
[52] U.S. Cl. ........................... 606/148; 606/194; 604/96; 600/18
[58] Field of Search ............................ 606/148, 194; 600/18; 604/96

[56] References Cited

U.S. PATENT DOCUMENTS

| | | |
|---|---|---|
| 4,312,353 | 1/1982 | Shahbabian . |
| 4,892,099 | 1/1990 | Ohkawa et al. ............... 600/156 |
| 4,943,275 | 7/1990 | Stricker .......................... 606/194 |
| 5,263,928 | 11/1993 | Trauthen et al. ............... 600/156 |
| 5,275,622 | 1/1994 | Lazarus et al. ................. 606/153 |
| 5,489,256 | 2/1996 | Adair ............................. 600/133 |

FOREIGN PATENT DOCUMENTS 83830164  5/1988  European Pat. Off. .

*Primary Examiner*—Gary Jackson
*Attorney, Agent, or Firm*—Benjamin J. Barish

[57] ABSTRACT

A surgical implement for use in suturing an annular part of a first organ to a second organ around an opening in the second organ includes a holder including a handle graspable by a user, and a stem insertable into the annular part of the first organ; and an inflatable balloon carried by the stem dimensioned such that in the deflated condition of the balloon the balloon and stem are insertable into the annular part of the first organ, and in the inflated condition of the balloon the balloon firmly engages the inner surface of the annular part of the first organ to hold it during suturing thereof to the first organ. One embodiment is described for use in coronary bypass surgery, and a second embodiment is described for use in valve replacement surgery.

28 Claims, 9 Drawing Sheets

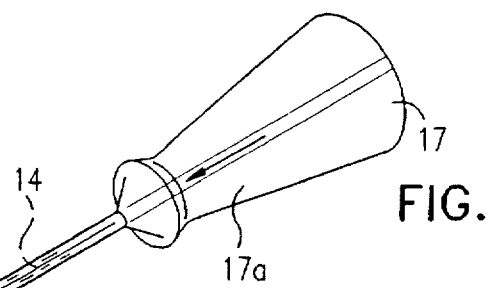
FIG. 3
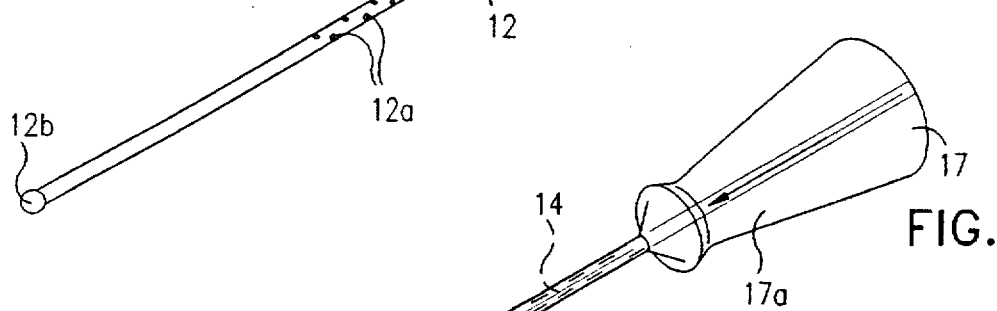
FIG. 3a
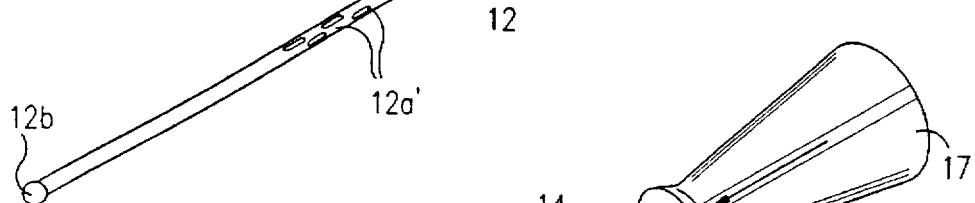
FIG. 4
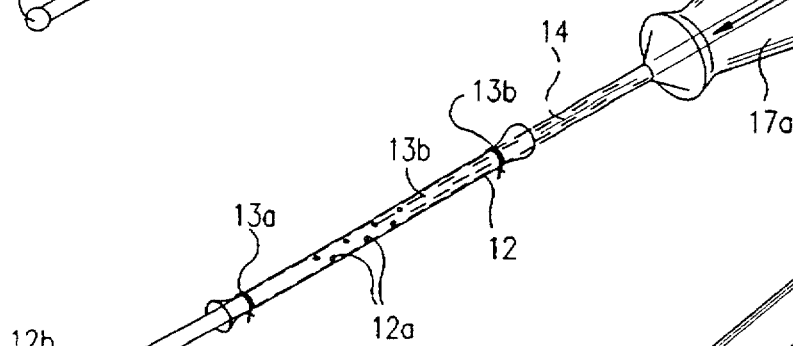
FIG. 5
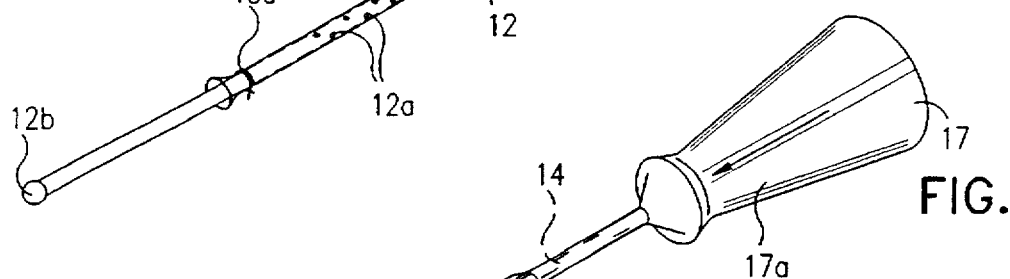
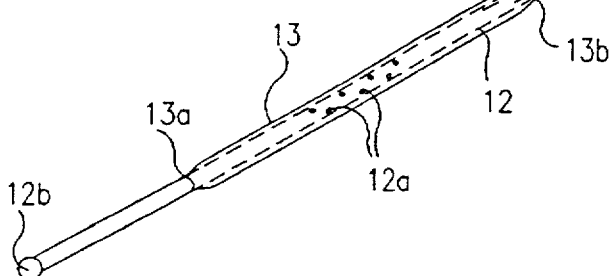

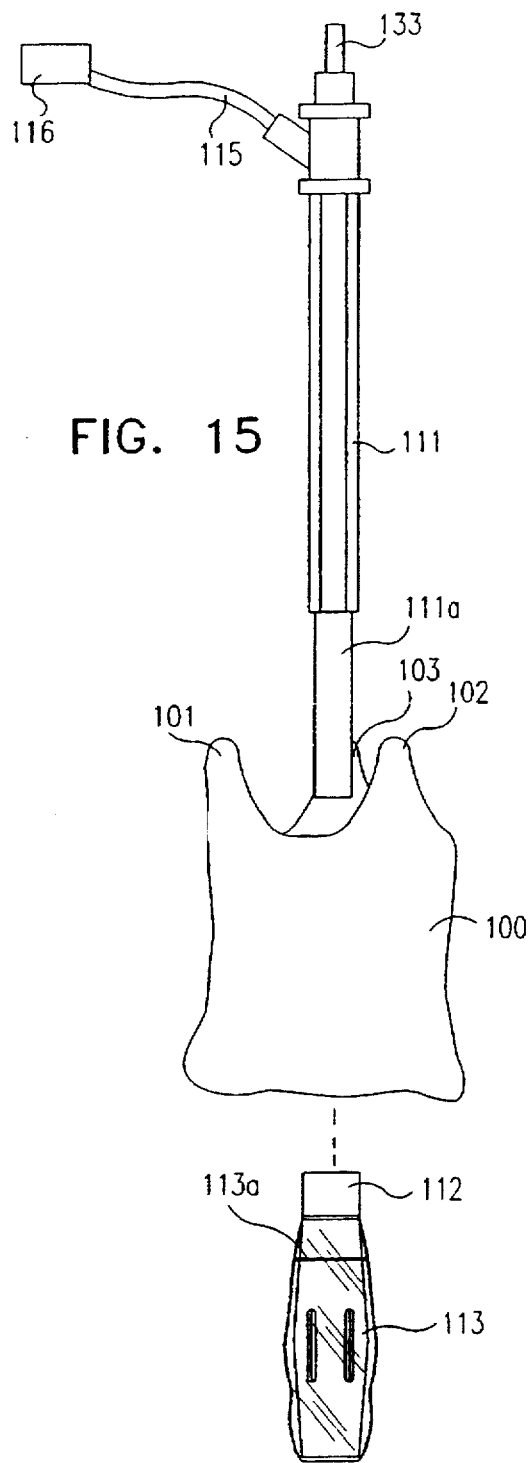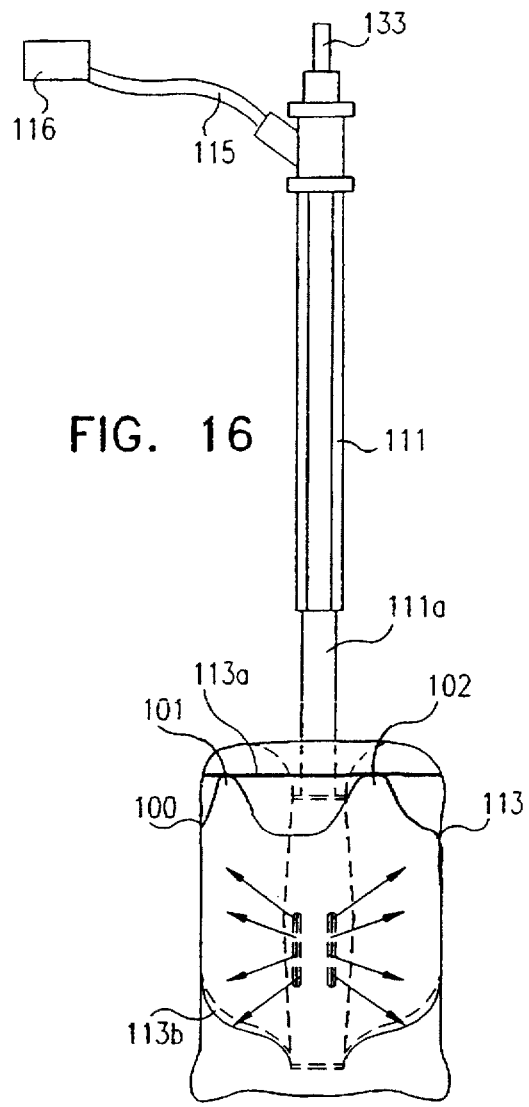

5,797,930

SURGICAL IMPLEMENT AND METHOD OF SUTURING

FIELD AND BACKGROUND OF THE INVENTION

The present invention relates to a surgical implement for use in suturing a first organ to a second organ. The invention is particularly useful for suturing a first blood vessel to a second blood vessel, for example in coronary bypass surgery and in valve replacement surgery. The invention is therefore described particularly with respect to these applications but it will be appreciated that it may also be used in other applications as well.

The invention also relates to a method of suturing, particularly to a method of making use of the novel surgical implement.

Coronary bypass surgery and valve replacement surgery require cardiac arrest for a significant period of time which should be minimized as much as possible to reduce the danger of death, damage to the heart, and/or post-operative complications. Such surgery also requires a high degree of skill and experience in applying the sutures in an even and symmetrical manner without damage to the organ being sutured, particularly blood vessels handled in a coronary bypass operation.

OBJECTS AND BRIEF SUMMARY OF THE INVENTION

An object of the present invention is to provide a surgical implement particularly useful in such surgical operations in order to minimize the period of cardiac arrest, and also to provide the above advantages as well as other advantages as will be described more particularly below. Another object of the invention is to provide a suturing method particularly useful in the above surgical procedures.

According to one aspect of the present invention, there is provided a surgical implement for use in suturing an annular part of a first organ to a second organ around an opening in the second organ, comprising a holder having a proximate end and a distal end. The holder includes a handle at the proximate end graspable by a user, and a stem at the distal end insertable into the annular part of the first organ. The stem includes a fluid passageway therethrough closed at a distal end of the stem and communicating with a plurality of openings formed through the stem inwardly of its closed distal end. An inflatable balloon is carried by the stem on its outer surface. The bellows is in the form of an elastomeric sleeve fixed at its opposite ends to the outer surface of the stem on opposite sides of the openings and is dimensioned such that in the deflated condition of the balloon, the balloon and stem are insertable into the annular part of the first organ, and in the inflated condition of the balloon, the balloon firmly engages the inner surface of the annular part of the first organ to hold it during suturing thereof to the second organ.

One preferred embodiment is described for use in coronary bypass surgery. In this embodiment, the stem and the balloon are of a size for insertion into the open end of a first blood vessel (e.g., a vein), constituting the annular part of the first organ, for securing the first blood vessel to a second blood vessel (e.g., the aorta or coronary artery), constituting the second organ.

A second preferred embodiment is described for use in valve replacement surgery. In this embodiment, the stem and balloon are of a size for insertion into a heart valve, constituting the first organ, to be implanted into an excised annulus in a subject's heart, consituting the second organ.

As will be described more particularly below, the use of such a surgical implement in the above-mentioned surgical operations enables a significant reduction to be made in the period of cardiac arrest, thereby reducing the danger of death, heart damage, or post-operative complications. Moreover, the use of such a surgical implement also greatly facilitates the application of the sutures in an even and symmetrical manner. It also reduces possible damage to the organ being sutured, particularly where the organ is a blood vessel whose ends are pliant, delicate and highly susceptible to damage when handled by forceps.

According to another aspect of the present invention, there is provided a method of suturing an annular part of a first organ to a second organ around an opening in the second organ, comprising: providing a holder having a central stem, a fluid passageway therethrough closed at one end, a plurality of openings through the stem inwardly of its closed end, and an elastomeric sleeve fixed at its opposite ends to the outer surface of the stem on opposite sides of the openings to define an inflatable balloon; inserting the holder, with the balloon in deflated condition, into the annular part of the first organ such that the balloon is aligned with an inner region of the first organ annular part and is spaced from an outer margin thereof between the inner region and the outer edge of the annular part; inflating the balloon such that its outer surface firmly engages the inner surface of the first organ annular part at said inner region thereof; suturing the outer margin of the first organ annular part to the second organ around the opening in the second organ; and removing the holder with the balloon from the first organ.

One described embodiment relates to coronary bypass surgery in which the first and second organs are first and second blood vessels. In this embodiment, while the balloon is inflated, the first blood vessel is tied to the holder at a location between the outer margin and the outer edge thereof, and is lightly tensioned to facilitate suturing the outer margin to the second blood vessel. In addition, the first blood vessel is formed with an axial slit extending from the outer edge to a location within the outer margin, to facilitate suturing the outer margin to the second blood vessel around the opening therein.

In accordance with further important features in this embodiment, one edge of the axial slit in the first blood vessel is sutured to the edge of one-half of the opening in the second blood vessel while the holder and its inflated balloon are located within the first blood vessel; the first blood vessel is then cut away from the holder such that the other edge of the axial slit is of a length substantially equal to the remainder of the edge of the opening in the second blood vessel; the holder and balloon are removed from the first blood vessel; the other edge of the axial slit of the first blood vessel is sutured to the second blood vessel; and the open end of the first blood vessel is sutured closed.

A second embodiment is described applicable to valve replacement surgery in which the first organ is preferably a stentless valve, or homograft valve to be transplanted into an excised annulus in a subject's heart, constituting the second organ.

Further features and advantages of the invention will be apparent from the description below.

BRIEF DESCRIPTION OF THE DRAWINGS

The invention is herein described, by way of example only, with reference to the accompanying drawings, wherein:

3

Figure 1:
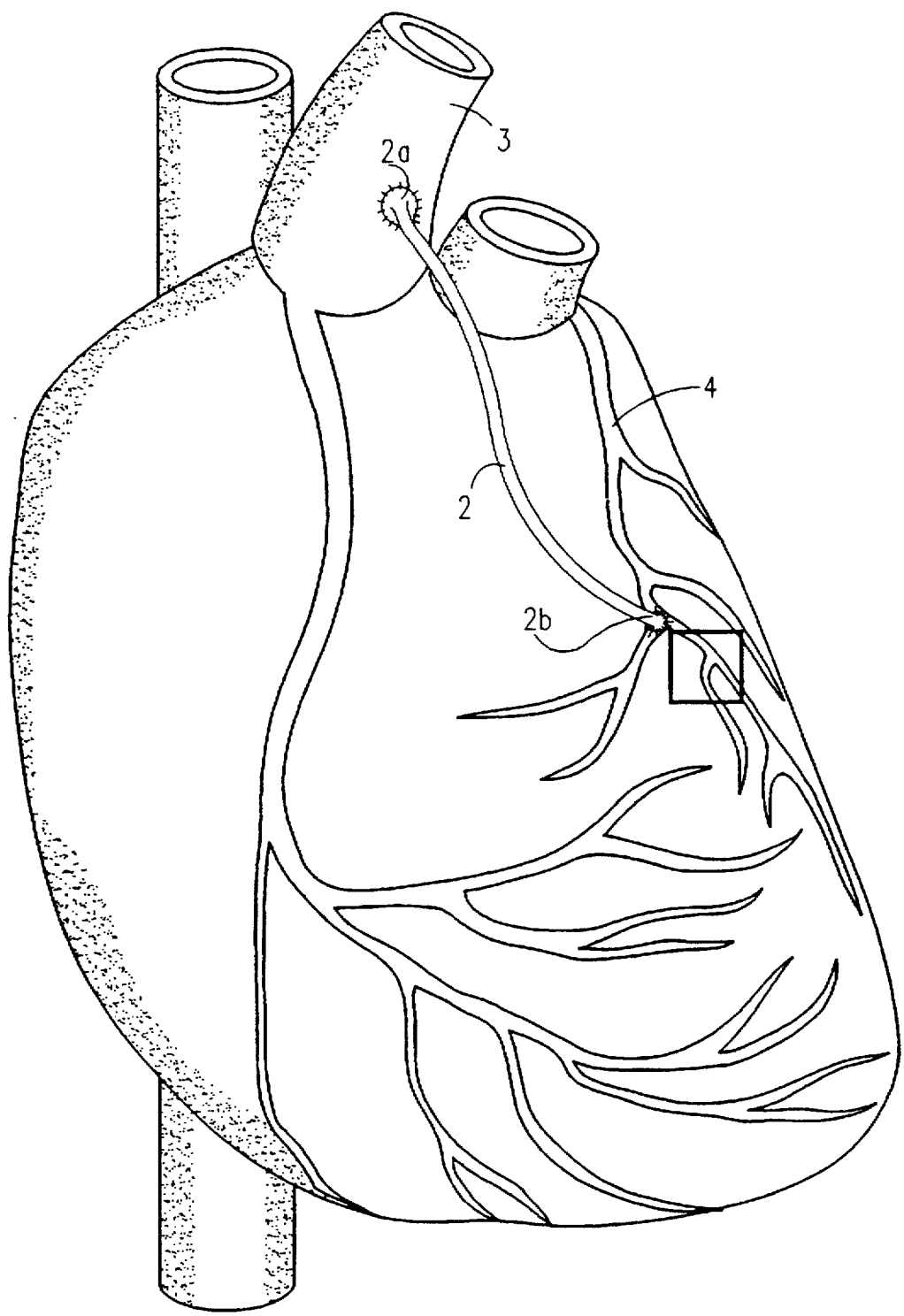
Figure 2:
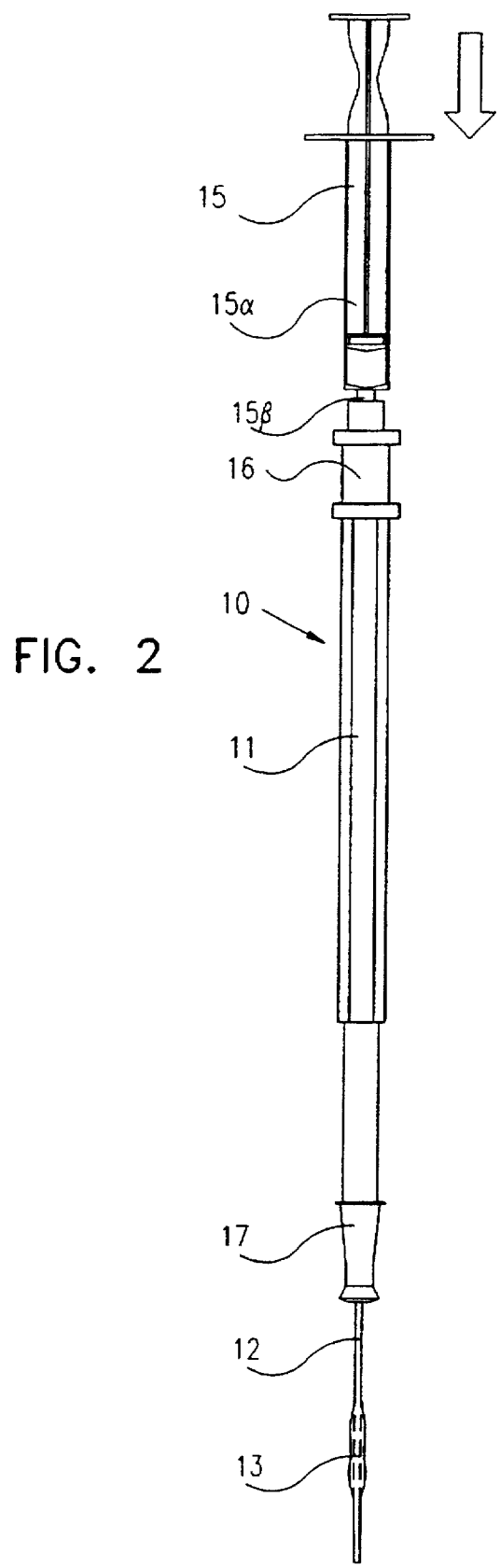
Figure 5A:
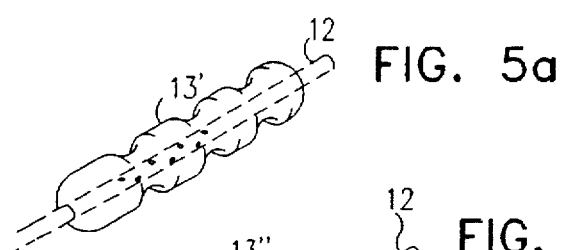
Figure 5B:
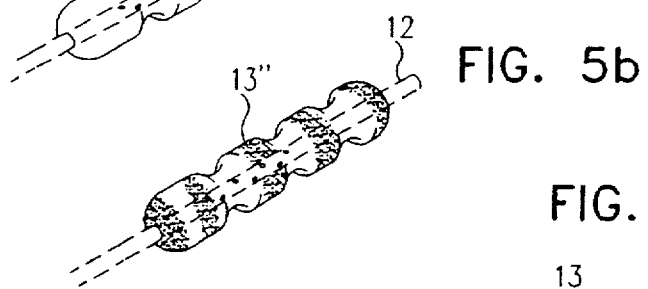
Figure 6:
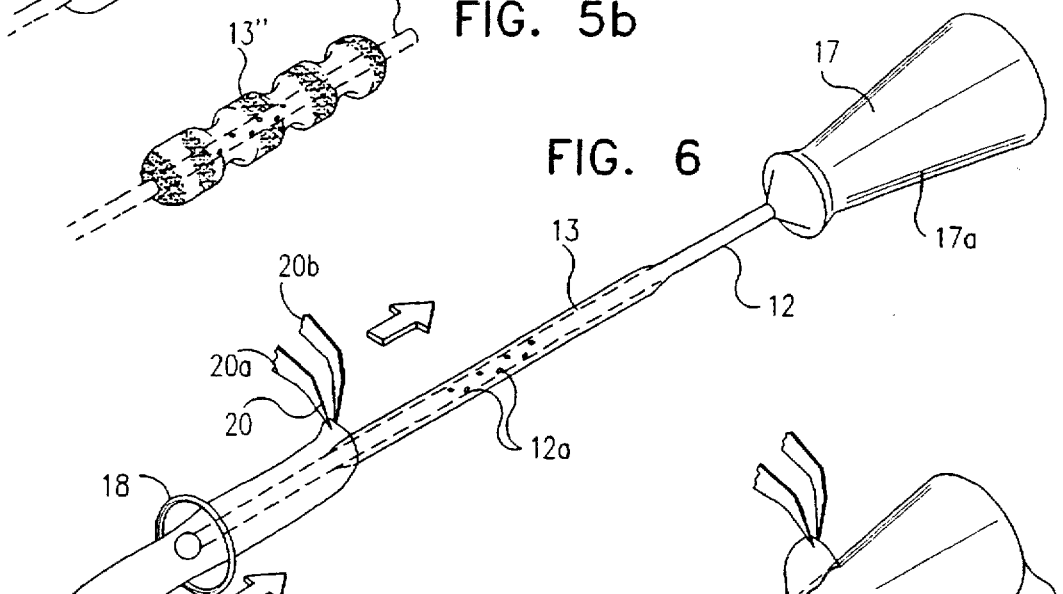
Figure 11:
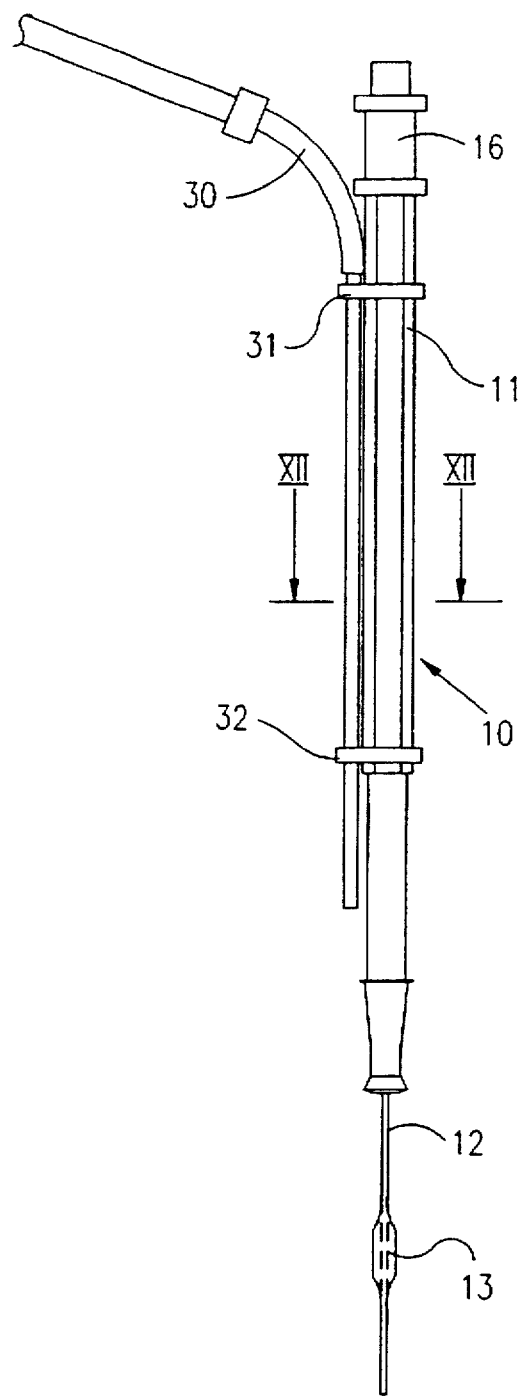
Figure 12:
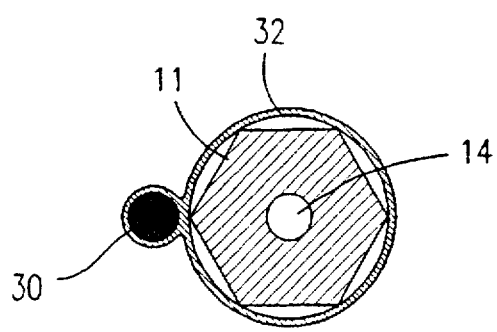
Figure 12A:
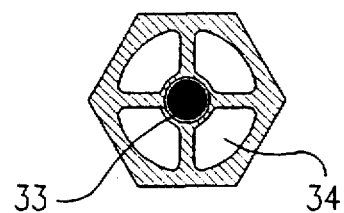
Figure 13:
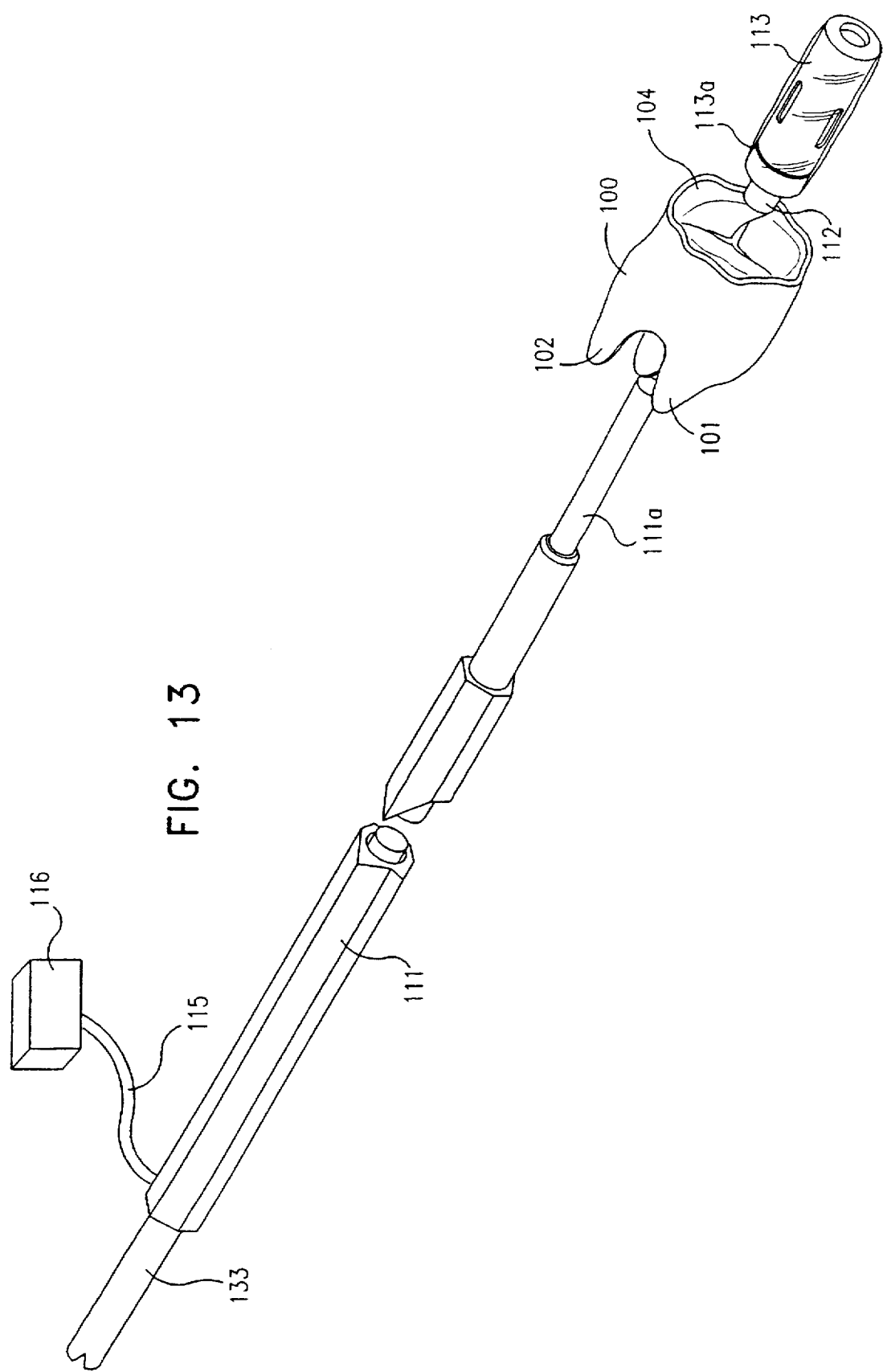
Figure 14:
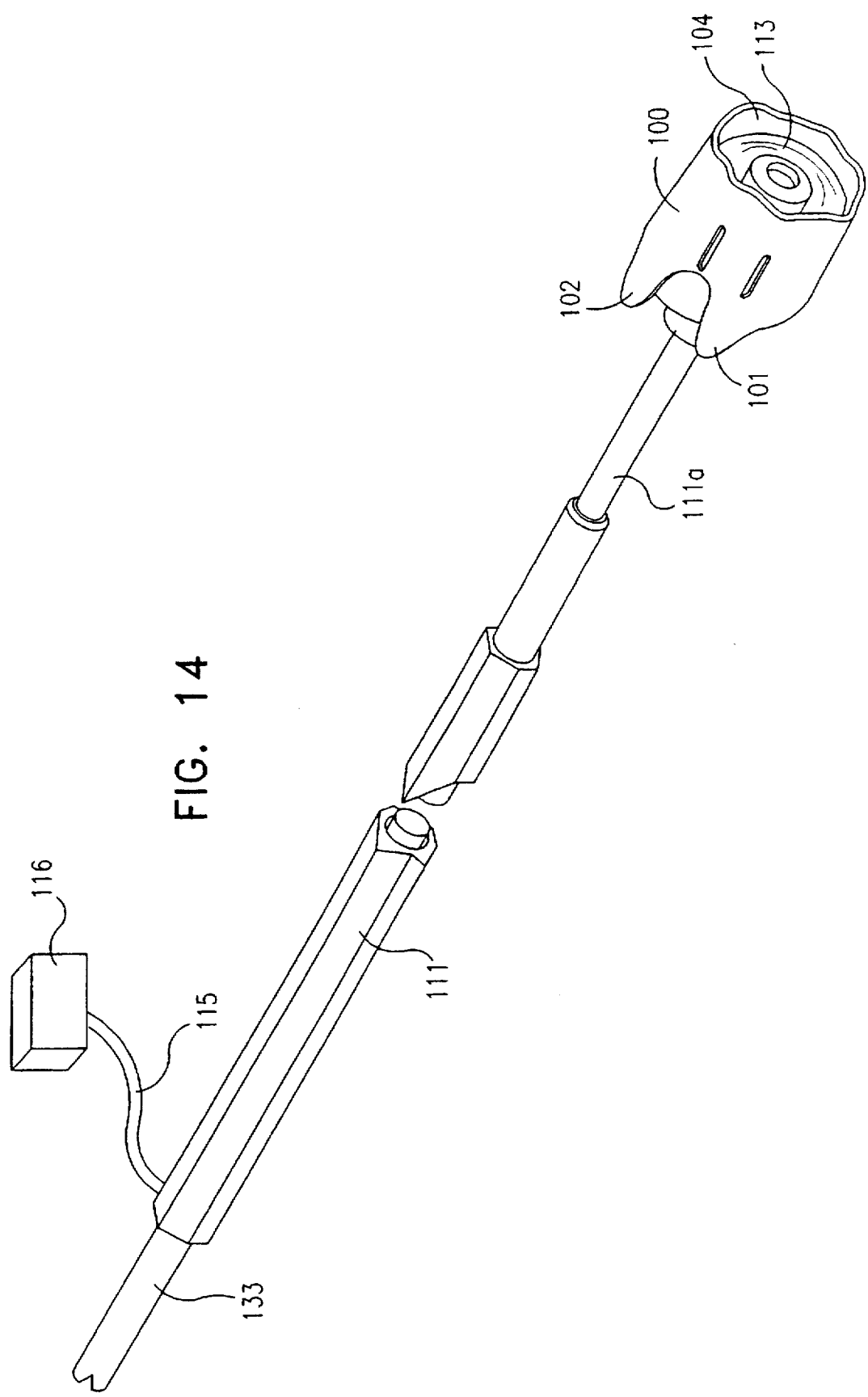

FIG. 1 is a diagram illustrating a human heart showing one coronary bypass performed thereon;

FIG. 2 is a side elevational view illustrating a surgical implement constructed in accordance with the present invention particularly useful in the coronary bypass surgery shown in FIG. 1;

FIGS. 3, 4 and 5 are views illustrating three conditions of the surgical implement of FIG. 2 during coronary bypass surgery, FIGS. 3a, 5a and 5b corresponding to FIGS. 3 and 5, respectively, but illustrating modifications in the construction of the surgical implement;

FIGS. 6-10 illustrate various stages in the coronary bypass surgery using the implement of FIG. 2;

FIG. 11 is a side elevational view illustrating a surgical implement according to FIG. 2 but equipped with an illuminator for illuminating the working site;

FIG. 12 is a sectional view along line XII—XII of FIG. 11;

FIG. 12a is a sectional view corresponding to that of FIG. 12 but illustrating a modification in the construction of the surgical implement;

FIGS. 13 and 14 are three-dimensional exploded and assembled views, respectively, illustrating another form of surgical implement constructed in accordance with the present invention particularly useful as a valve holder in valve-replacement surgery;

and FIGS. 15 and 16 are views corresponding to FIGS. 13 and 14, but illustrating the surgical implement with the balloon in its inflated condition for firmly holding the valve to facilitate its being sutured in a excised annulus in the heart.

DESCRIPTION OF PREFERRED EMBODIMENTS

The Embodiment of FIGS. 1-10

FIG. 1 illustrates a single coronary bypass performed on a human heart by grafting a vein 2 between the aorta 3 and coronary artery 4. It will be appreciated that the illustration in FIG. 1 of a single bypass is only for simplicity purposes since the usual bypass surgery normally involves a plurality of bypasses, typically four or five. It will also be appreciated that arteries are sometimes used instead of veins. In the single bypass illustrated in FIG. 1, one end 2a of vein 2 is sutured around an opening in the aorta 3, and the opposite end 2b is sutured around an opening in the coronary artery 4.

Heretofore, each end 2a, 2b of the vein 2 was sutured by holding the respective end with forceps while applying the suture needle to produce a continuous stitch of many loops (typically about sixteen loops) according to the size of the vein (or artery) used in the bypass. Such a suturing procedure is very time-consuming and difficult to perform. Other drawbacks include the danger of damage to the pliant and delicate ends of the vein being handled by the forceps, the awkwardness in suturing the end of a vein while manipulating it with forceps, the difficulty in producing evenly-spaced stitches symmetrically around the opening in the artery, and the danger of stitching errors such as posterior wall hooking. Also, it is very difficult with the existing technique to create a juncture, or anastomosis, of the desirable cobra-head configuration at each of the sutured ends of the vein 2 to minimize obstruction of blood flow.

As will be described below, the surgical implement illustrated in FIG. 2 facilitates suturing each of the two ends 2a,

4

2b of the vein 2 in a manner which has advantages in the above respects.

The illustrated implement includes a holder, generally designated 10, having a handle 11 at the proximal end graspable by a user, and a stem 12 at the opposite, distal end insertable into the respective open end of the vein 2 (or artery) to be sutured. An inflatable balloon 13 is carried by stem 12 on its outer surface. Balloon 13 is dimensioned such that, in its deflated condition it is insertable with the stem into the respective end of the vein 2, and in its inflated condition it firmly engages the inner surface of the end of the vein to hold it during the suturing operation. Stem 12 is formed with a fluid passageway 14 (e.g., FIGS. 3–5) for inflating and deflating the balloon. Passageway 14 communicates with a plurality of openings 12a formed through the stem 12 in the area of the stem covered by the balloon 13, but terminates short of the distal tip 12b of the stem. In FIG. 3, openings 12a are of circular configuration, whereas in the modification of FIG. 3a, the openings 12a' are of rectangular configuration.

Balloon 13 is inflated by a removable inflating device in the form of a conventional syringe 15 (FIG. 2) having a nipple 15 at one end, and a manual plunger 15 for forcing a fluid via the nipple and passageway 14 to inflate the balloon. Preferably, the fluid is saline water, but could be other fluids, such as air.

The implement illustrated in FIG. 2 also includes a one-way valve 16 at the outer (proximal) end of handle 11 communicating with passageway 14. Valve 16 has a socket for receiving nipple 15. Depressing plunger 15 forces the fluid through the valve to inflate the balloon, and removal of the syringe closes the valve to prevent deflation of the balloon. When the balloon is to be deflated, the nipple 15 of the syringe is reinserted into valve 16, which thereby opens the valve to permit the deflation of the balloon.

The distal tip 12b of stem 12 is of a rounded enlarged configuration to facilitate insertion of the stem into the respective end of the vein 2 (or artery). The proximal end 12 of stem 12 is fixed to a head 17 removably attachable to handle 11.

Balloon 13 is in the form of an elastomeric sleeve received over the outer surface of stem 12 and fixed thereto, as by adhesive, at its two ends 13a, 13b on opposite sides of the fluid openings 12a in the stem. As shown in FIG. 5, balloon 13, in its inflated condition, is of an elongated cylindrical configuration so as to enable it to firmly hold the open end of the vein (or artery). FIG. 5a illustrates a modification wherein the balloon 13', in its inflated condition, has an outer surface of ripple or corrugated configuration; and FIG. 5b illustrates another modification wherein the balloon 13" has a roughened outer surface. Either modification may be used to further enhance the capability of the inflated balloon to hold the open end of the vein (or artery).

The outer surface 17a of head 17 is of conical configuration to facilitate the insertion of the head, including its stem 12 and balloon 13, into the respective end of the vein 2 to be sutured. After the head 17 has been so inserted, the end of the vein is fixed to head 17 by a locking ring 18 which is moved inwardly of the head to become wedged against its outer conical surface 17a.

Before the vein (or artery. ) is applied to the head 17, the respective end of the vein is formed with a slit 20, extending axially inwardly from the outer edge of the vein to a location between locking ring 18 and the inflatable balloon 13. As will be described more particularly below, slit 20a formed in the respective end of the vein not only facilitates the application of the vein to the head 17 before its balloon 13 is inflated, but also facilitates suturing the vein after the balloon has been inflated.

FIGS. 6–10 illustrate a preferred manner of using the implement of FIG. 2 for suturing one end of vein 2 to the respective blood vessel, in this case to the coronary artery 4 (FIG. 1). For this purposes, the coronary artery is formed with an opening 4a (FIG. 9), and the respective end of the vein is formed with the previously-mentioned axial slit 20 having the two edges 20a, 20b.

Figure 7:
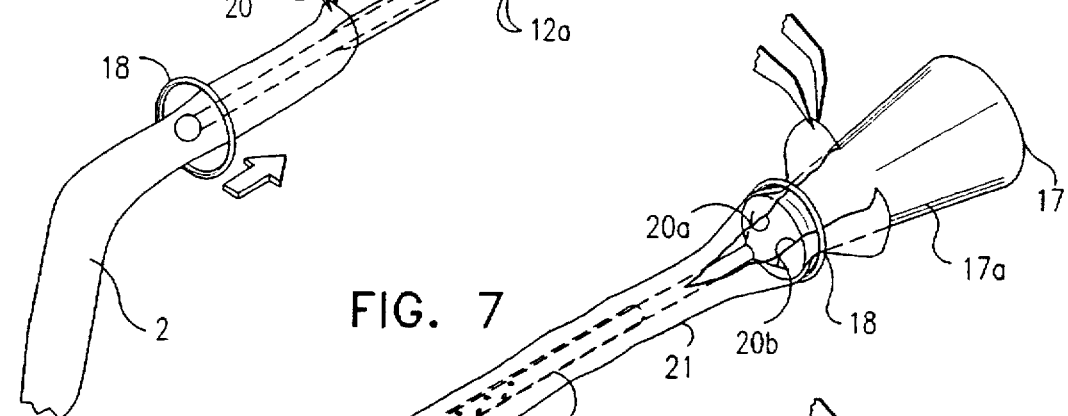

With the head 17 applied to handle 11, and with balloon 13 in its deflated condition (FIG. 6), the respective end of the vein 2 is inserted over the conical surface 17a of the head 17 to the position illustrated in FIG. 7 wherein the balloon 13 is spaced from the slit 20 in the vein by an unslitted region 21. Retainer ring 18 is then moved over the outer surface of the vein end to fix, by a wedging action, that end of the vein to the conical surface 17a of head 17.

Figure 8:
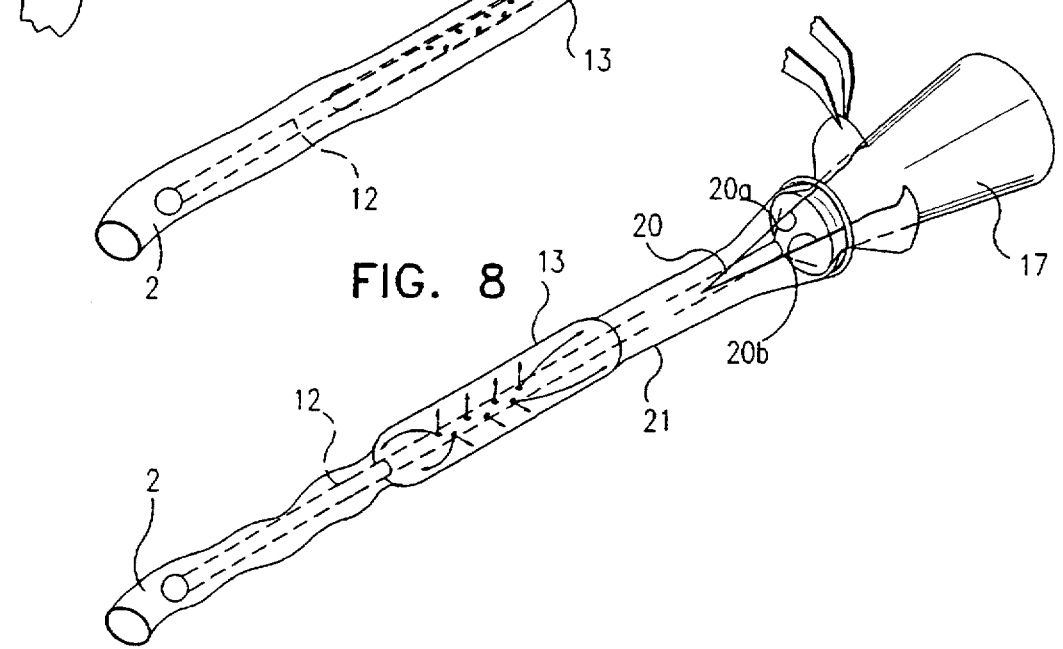

A small pull force may be applied (leftwardly, FIG. 8) to lightly tension end portion 21 of the vein fixed by ring 18. Balloon 13 may then be inflated, by passing a fluid (saline water, air, etc.) via passageway 14 and stem openings 12a into the region between the outer surface of stem 12 and the inner surface of the balloon 13, to firmly engage the inner surface of the vein 2 (FIG. 8).

Figure 10:
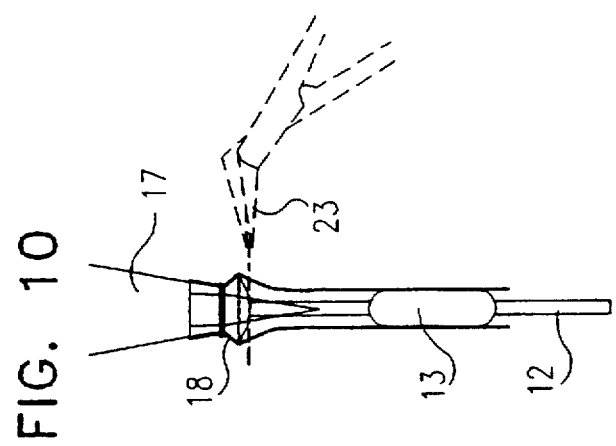
Figure 9:
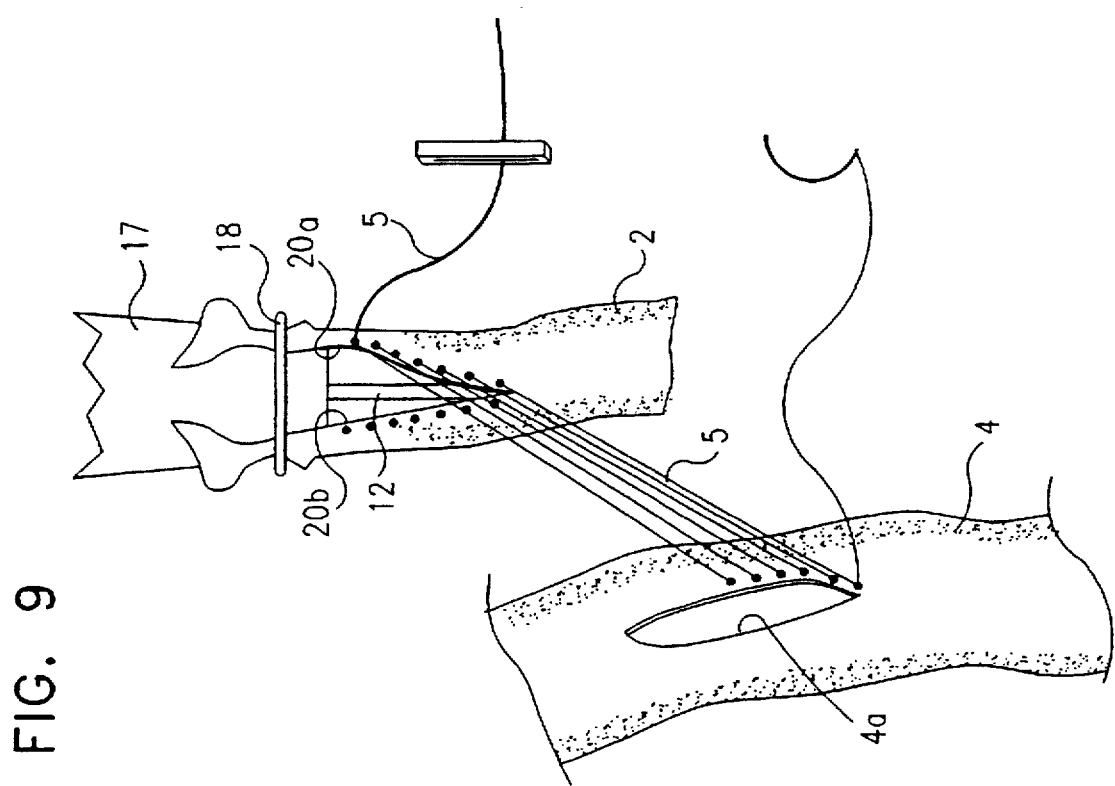

The end of the vein, when so held by the inflated balloon 13, may then be conveniently located adjacent to the suturing site and sutured to opening 4a in coronary artery 4 in the following manner as shown in FIGS. 9 and 10:

First, one side 20a of the axial slit 20 formed in the respective end of the vein (or artery) is sutured by sutures 5 to one-half the periphery of opening 4a while the vein is retained on head 17 by the inflated balloon 13 and is lightly tensioned by a pull force 19 (FIG. 9). After one-half of the respective end of the vein has thus been sutured, the vein is severed, as shown schematically at 23 in FIG. 10, along an annular line slightly inwardly of the retainer ring 18, and the open end of the vein so produced is then sutured closed.

The severing of the vein from head 17 permits the head, and its stem 12 and balloon (now deflated) 13, to be withdrawn from the interior of the vein 2. However, since one half of the vein (edge 20a of slit 20) has already been sutured to one half the periphery of opening 4a in the coronary artery 4, the vein remains in place adjacent to the coronary artery, such that the other half of the vein (FIG. 20b of slit 20) may now be conveniently sutured to the remaining half of the periphery of opening 4a.

An important advantage in the above-described technique is that, after edge 20a of the vein has been sutured to about one-half the periphery of opening 4a, the surgeon can sever the vein, as shown at 23 in FIG. 10, along a line such that the axial length of the remaining edge 20b is substantially equal to the remainder of the edge of opening 4a to be sutured, thereby better assuring an even and symmetrical application of the suture loops around opening 4a, and better chances of obtaining the desirable cobra-head configuration of the sutured juncture.

In a multiple bypass, the distal ends of all the veins used in the multiple bypass are sutured to the respective coronary arteries while the heart is arrested. Therefore, it is critical to minimize as much as possible the time taken for suturing the distal ends of the veins. After the distal ends of the veins have been sutured, the heart is resuscitated, and the same procedure as described above is followed for suturing the proximal ends of the veins to the aorta.

It will be seen that the illustrated implement, and the surgical technique utilizing that implement, provide a number of important advantages when suturing a blood vessel to other blood vessels, such as in coronary bypass surgery. Thus, it widely opens the end of the vein (or artery) to be sutured such as to facilitate suturing the vein in a manner avoiding or minimizing contacting the vein with forceps. The illustrated implement also supports the pliant and delicate ends of the veins in a manner which minimizes the possibility of damage to them, as compared for example when forceps are used for this purpose. The use of this implement also enables the surgeon, during the course of the operation, to trim the end of the vein in such manner as to produce a more even positioning of the suture loops. It will then be seen that this implement, particularly when used in the above-described technique, facilitates the application of the sutures, minimizes the suturing time, improves accuracy, reduces the possibility of errors such as posterior wall hooking, and better enables the surgeon to produce the desirable cobra-head juncture at the sutured juncture thereby minimizing obstruction of blood flow.

Preferably, the head 17, stem 12, and balloon 13, would be supplied for one-time use, according to various sizes corresponding to different size veins (or arteries) to be sutured. The handle 11, however, would preferably be supplied for multiple use by making it quickly attachable to and detachable from head 17 whenever a new head is to be applied.

The Embodiment of FIGS. 11–12a

FIGS. 11 and 12 illustrate the surgical implement of FIGS. 2–10 equipped with an illuminator for illuminating the working site during coronary bypass surgery. Thus, the implement is basically the same as described above, and therefore its corresponding parts are identified by the same reference numerals. FIGS. 11 and 12 illustrate the illuminator in the form of an optical fiber 30 fixed to the outer surface of handle 11 by a pair of rings 31, 32 and extending along the outer surface of the handle. FIG. 12a illustrates a variation wherein the optical fiber 33 passes through the interior of handle 11, the latter handle being formed with one or more fluid passageways 34 for inflating the balloon.

The Embodiment of FIGS. 13–16

FIGS. 13–16 illustrate a suturing implement in the form of a valve holder constructed in accordance with the present invention for use in suturing a prosthetic valve 100, particularly a stentless or homograft tissue valve, during valve-replacement surgery. In this case, the stem 112, and the inflatable balloon 113 carried by the stem, are dimensioned such that when the balloon 113 is deflated, it and its stem are insertable into the valve 100; and when the balloon is inflated, the balloon firmly engages the valve to hold it in place during the suturing operation.

At the present time, the use of stentless valves in valve-replacement surgery involves a number of difficulties to the surgeon which have greatly limited the use of such valves despite their advantages over stented valves. Thus, the matching of the size of the valve with the size of the excised annulus is critical, but is extremely difficult with a stentless valve as compared to a stented valve. Moreover, stentless valves are very difficult to hold and to manipulate during the suturing operations; also, there is a very substantial risk of accidentally perforating a cusp which would destroy the effectiveness of the valve. These difficulties are substantially overcome or significantly reduced by the use of the valve holder illustrated in FIGS. 13–16.

As shown in FIGS. 13 and 15, the stem 112, and the balloon 113 carried by the stem, are constructed as a separate unit or head which is quickly attachable to handle 111 and conveniently applied so as to be at a predetermined position with respect to the valve to be sutured. For this purpose, the inner end 111a of handle 111 is formed with an axial bore or socket 120 dimensioned to permit stem 112 to be inserted therein to a selected axial position with respect to the longitudinal axis of the handle, and to be retained therein by an O-ring 121. The balloon 113 is preferably marked with an annular line 113a to be aligned with the outer edges of the flaps 101–103 of the valve when the stem 112 is attached to the handle 111.

In use, stem 112, including its balloon 113 in deflated condition, is applied through the lower end of the valve 100 (FIG. 15) to the axial position wherein line 113a on the balloon is aligned with the upper edges of the flaps 101–103, and the lower end of the balloon is inwardly spaced from the lower end of the valve 100 (FIGS. 14–16). The balloon 113 is then inflated to engage the inner surface of the valve and to firmly hold it during the suturing of the valve in the excised annulus by passing the sutures through the lower end 104 of the valve not engaged by the balloon 113.

Preferably, the lower end of the balloon, shown at 113b in FIG. 16, is of larger thickness than the remainder of the balloon to prevent that end of the balloon from projecting outwardly of the valve when the balloon is inflated. This provides a free area 104 of the valve for receiving the sutures; it also decreases the possibility of puncturing the balloon during the suturing operation. The actual suturing may be done in a conventional manner, e.g., by applying separate sutures to area 104 of the valve, sliding the valve into the excised annulus, and then tying and trimming the sutures.

If the illustrated holder is used for a mitral valve, the lower section 111a of handle 111 is preferably bendable with memory (i.e., it retains its bent shape) to facilitate handling the mitral valve.

It will thus be seen that the valve holder illustrated in FIGS. 13–16 provide a number of important advantages when using stentless valves in valve-replacement surgery. Since the inflated balloon 113 firmly holds the valve in an open condition, the surgeon is better able to determine whether the valve truly matches the size of the excised annulus before the suturing actually starts; if it does not, the surgeon can select another size stentless valve if available, or a stented valve if necessary. Also, inserting the stem and balloon into the valve via its lower end decreases the possibility of damage to the cusps, and also covers the cusps during the suturing operation thereby decreasing the possibility of perforating the cusps. Further, since the inflated balloon provides a large smooth surface of contact with the valve, there is less danger of damaging the valve (e.g., as compared to forceps) during the valve handling and suturing operations. In addition, the line marking 113a on the balloon permits proper alignment of the balloon with respect to the valve.

The balloon 113 is preferably colored to increase its visibility in the suturing operation, but it may also be transparent. The balloon is preferably made of a medically-approved elastomeric material. The stem is preferably made of stainless steel or any medically approved plastic material.

The valve holder illustrated in FIGS. 13 and 14 may also include an illuminator, shown in the form of an optical fiber 133 extending through the handle 111 for illuminating the working site.

Another change in the implement illustrated in FIGS. 13 and 14 is that its balloon 113 is inflated by means of a flexible tube 115 coupled to handle 111. This flexible tube includes the one-way valve 116, corresponding to valve 16 in FIG. 2, permitting inflation of the balloon 113 by a syringe-type inflating device as described above, or other type inflating device.

In all other respects, the implement illustrated in FIGS. 13–16 is constructed and operates in substantially the same manner as described above with respect to the implement of FIG. 2.

The implement can also be used for indicating the size of the excised annulus and the volume of the syringe needed to inflate the balloon to the required size when implanting the valve. Thus, after the annulus in the heart has been excised, the implement, without the valve and with the balloon deflated, may be introduced into the excised annulus and the balloon then inflated to measure the size of the excised annulus, and also to indicate the syringe volume needed to inflate the balloon to the required size. This information can then be used for selecting the appropriate size valve, and also for depressing the syringe plunger to inflate the balloon to the volume required to hold the valve while applying it by the implement into the excised annulus for suturing.

While the invention has been described with respect to two preferred embodiments, it will be appreciated that these are set forth merely for purposes of example, and that many other applications of the invention could be made. For example, the implement could be used for suturing other organs, such as intestine, peripheral vascular arteries, peripheral vascular prosthetic grafts of various materials, etc., particularly where the device includes an annular section which is pliant and delicate such that handling it with forceps is not only awkward but may also damage the organ. Further, the implement could be used without the illustrated illuminators, or with other types of illuminators. Many other variations, modifications and applications of the invention will be apparent.

I claim:

1. A surgical implement for use in suturing an annular part of a first organ to a second organ around an opening in the second organ, comprising:

a holder having a proximate end and a distal end;

said holder including a handle at said proximate end graspable by a user, and a stem at said distal end insertable into said annular part of the first organ;

said stem including a fluid passageway therethrough closed at a distal end of the stem and communicating with a plurality of openings formed through the stem inwardly of said closed distal end thereof;

and an inflatable balloon carried by said stem on the outer surface thereof;

said balloon being in the form of an elastomeric sleeve fixed at its opposite ends to the outer surface of said stem on opposite sides of said opening and being dimensioned such that in the deflated condition of the balloon the balloon and stem are insertable into said annular part of the first organ, and in the inflated condition of the balloon the balloon firmly engages the inner surface of the annular part of the first organ to hold it during suturing thereof to said second organ.

2. The implement according to claim 1, wherein said stem is rigid.

3. The implement according to claim 1, wherein the outer tip of said distal end of the stem is of a rounded enlarged configuration to facilitate insertion of the stem and balloon into said first organ.

4. The implement according to claim 1, wherein said stem and balloon are joined together as a unit which unit is removable from said handle to permit multiple use of the handle with one time use of the stem and balloon unit.

5. The implement according to claim 1, wherein said holder further includes an optical fiber carried by said handle for conducting light to illuminate the working site during the suturing of said first organ to said second organ.

6. The implement according to claim 5, wherein said optical fiber is fixed to and extends along the outer surface of said handle.

7. The implement according to claim 5, wherein said optical fiber extends through the interior of said handle.

8. The implement according to claim 1, wherein said passageway includes a one-way valve permitting inflation of the balloon, which one-way valve is manually releasable to deflate the balloon.

9. The implement according to claim 8, further including a removable inflating device having a nipple received in an opening in said one-way valve for opening said valve, and a manual plunger for forcing a fluid through the one-way valve to inflate said balloon.

10. The implement according to claim 1, wherein said stem and said balloon are of a size for insertion into the open end of a first blood vessel, constituting said annular part of the first organ, for suturing the first blood vessel to a second blood vessel, constituting said second organ.

11. The implement according to claim 10, wherein said balloon in its inflated condition has an outer surface of ripple configuration.

12. The implement according to claim 10, wherein said balloon has a roughened outer surface.

13. The implement according to claim 10, wherein the outer surface of said holder is of conical configuration to facilitate receiving the end of said first blood vessel to be sutured to said second blood vessel.

14. The implement according to claim 1, wherein said stem and balloon are of a size for insertion into a heart valve, constituting said first organ, to be implanted into an excised annulus in a subject's heart, consituting the second organ.

15. The implement according to claim 14, wherein the stem and balloon are formed as a separate unit attachable to the handle.

16. The implement according to claim 15, wherein the stem is attachable to said handle at different positions with respect to the longitudinal axis of the handle to permit aligning the balloon with respect to the valve.

17. The implement according to claim 16, wherein the balloon is formed with a marking to facilitate aligning it with the valve.

18. The implement according to claim 14, wherein said balloon includes a main part to be enclosed by the valve, and an end to be aligned with a lower end of the valve, said end being of larger thickness than the main part of the balloon, to prevent said end of the balloon, when inflated, from expanding through the lower end of the valve when the valve is held by the balloon.

19. A method of suturing an annular part of a first organ to a second organ around an opening in the second organ, comprising:

providing a holder having a central stem, a fluid passageway therethrough closed at one end thereof, a plurality of openings through the stem inwardly of its closed end, and an elastomeric sleeve fixed at its opposite ends to the outer surface of the stem on opposite sides of said opening to define an inflatable balloon;

inserting said holder, with said balloon in deflated condition, into said annular part of the first organ such that the balloon is aligned with an inner region of the first organ annular part and is spaced from an outer margin thereof between said inner region and the outer edge of said annular part;

inflating said balloon such that its outer surface firmly engages the inner surface of said first organ annular part at said inner region thereof;

suturing said outer margin of the first organ annular part to the second organ around said opening in the second organ;

and removing said holder with the balloon from said first organ.

20. The method according to claim 19, wherein said first and second organs are first and second blood vessels.

21. The method according to claim 20, wherein, while said balloon is inflated, the first blood vessel is tied to the holder at a location between said outer margin and said outer edge thereof, and said first blood vessel is tensioned between said outer margin and said tied location to facilitate suturing said outer margin to the second blood vessel.

22. The method according to claim 21, wherein said first blood vessel is formed with an axial slit extending from said outer edge to a location within said outer margin, to facilitate suturing said outer margin to the second blood vessel around the opening therein.

23. The method according to claim 22, wherein one edge of the axial slit in the first blood vessel is sutured to the edge of one-half of the opening in said second blood vessel while the holder and its inflated balloon are located within the first blood vessel; the first blood vessel is then cut away from the holder such that the other edge of the axial slit is of a length substantially equal to the remainder of the edge of the opening in the second blood vessel; the holder and balloon are removed from the first blood vessel; said other edge of the axial slit of the first blood vessel is then sutured to said second blood vessel and the open end of the first blood vessel is then sutured closed.

24. The method according to claim 19, wherein said first organ is a valve to be transplanted into an excised annulus in a subject's heart, constituting the second organ.

25. The method according to claim 24, wherein the stem and balloon are formed as a separate unit, and said unit is passed through the lower end of the valve to be attached to the handle.

26. In a method of surgery involving the preparation of an excised annulus for implanting a prosthetic device therein, the improvement of measuring the size of the excised annulus by applying a deflated balloon into the excised annulus, and inflating the balloon until it fills the excised annulus.

27. The method according to claim 26, wherein the prosthetic device is a valve to be implanted in the heart of a subject, and wherein said implement, including said balloon, is also used as a valve holder for holding the valve when the balloon is inflated.

28. The method according to claim 27, wherein when the balloon is used for measuring the size of the excised annulus, the volume needed for inflating the balloon until it fills the excised annulus is noted, and is used when inflating the balloon to hold the valve during the implanting of the valve.

* * * * *